United States Patent
Jennings, Jr. et al.

(10) Patent No.: US 6,331,309 B1
(45) Date of Patent: Dec. 18, 2001

(54) HYDROGEL COMPOSITIONS FOR THE CONTROLLED RELEASE ADMINISTRATION OF GROWTH FACTORS

(75) Inventors: Robert N. Jennings, Jr., San Jose; Bing Yang, Redwood City; Andrew A. Protter, Palo Alto; Yu-Chang John Wang, Los Altos, all of CA (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 09/390,164

(22) Filed: Sep. 3, 1999

Related U.S. Application Data

(60) Provisional application No. 60/099,168, filed on Sep. 4, 1998.

(51) Int. Cl.[7] .............................. A61F 13/00; A61K 9/70
(52) U.S. Cl. ........................ 424/422; 424/423; 424/426; 424/443; 424/484
(58) Field of Search ................................... 424/484, 422, 424/423, 426, 443

(56) References Cited

U.S. PATENT DOCUMENTS

| | | |
|---|---|---|
| 4,100,271 | 7/1978 | Krezanoski . |
| 5,013,769 | * 5/1991 | Murray et al. ........................ 424/434 |
| 5,100,668 | * 3/1992 | Edelman et al. ..................... 424/484 |
| 5,271,943 | * 12/1993 | Bogart et al. ........................ 424/484 |
| 5,457,093 | 10/1995 | Cini et al. . |
| 5,470,829 | 11/1995 | Prisell et al. . |
| 5,591,709 | * 1/1997 | Lindenbaum ........................ 424/484 |
| 5,705,485 | 1/1998 | Cini et al. . |
| 5,952,006 | * 9/1999 | Drizen et al. ........................ 424/484 |
| 6,045,814 | * 4/2000 | Roulier et al. ........................ 424/484 |
| 6,103,266 | * 8/2000 | Tapolsky ............................... 424/484 |

FOREIGN PATENT DOCUMENTS

| | | |
|---|---|---|
| 0 312 208 A | 4/1989 | (EP) . |
| 0 551 626 A | 7/1993 | (EP) . |
| 2 644 066 A | 9/1990 | (FR) . |

OTHER PUBLICATIONS

Ahn and Mustoe, Effects of Ischemia on Ulcer Wound Healing: A New Model in the Rabbit Ear, Plastic Surgery. 24:17–23 (1990).
Wu et al., Effects of Oxygen on Wound Responses to Growth Factors, Growth Factors. 12:29–35 (1995).
Aqualon® Sodium Carboxymethylcellulose Physical and Chemical Properties, Hercules Inc., Wilmington, DE.
Brookfield Digital Rheometer Model DV–III Operating Instructions Manual No. M/91–210–I297, Brookfield Engineering Laboratories.
Chemical Abstracts, vol. 124, No. 16, Apr. 15, 1996, Columbus, Ohio, US; Abstract No. 211858, Lee, Yoo–Cheol et al., "Formulation of water–soluble topical preparations of epidermal growth factor," XP002132165, abstract and Yakche Hakhoechi (1995), 25(3), 177–84.

* cited by examiner

Primary Examiner—Thurman K. Page
Assistant Examiner—S. Howard
(74) Attorney, Agent, or Firm—Knobbe, Martens, Olson & Bear, LLP

(57) ABSTRACT

Compositions and methods are disclosed for the controlled release delivery of polypeptide growth factors. The compositions of the invention are hydrogels which comprise: a polypeptide growth factor having at least one region of positive charge; a physiologically acceptable water-miscible anionic polymer; a physiologically acceptable non-ionic polymeric viscosity controlling agent; and water.

37 Claims, 6 Drawing Sheets

HYDROGEL COMPOSITIONS FOR THE CONTROLLED RELEASE ADMINISTRATION OF GROWTH FACTORS

CROSS-REFERENCE TO RELATED APPLICATIONS

This is a non-provisional application of co-pending provisional application Ser. No. 60/099,168 filed on Sep. 4, 1998, the disclosure of which is hereby incorporated by reference and to which application priority is claimed under 35 USC 119.

BACKGROUND OF THE INVENTION

This invention relates to formulations for the controlled delivery of growth factors. In specific embodiments, the invention relates to controlled release delivery of angiogenic growth factors for the treatment of ischemic tissue and/or for wound healing.

Polypeptide growth factors regulate the growth and proliferation of cells. A number of human growth factors have been identified and characterized. Merely by way of example, these include basic fibroblast growth factor (bFGF), acidic fibroblast growth factor (aFGF), vascular endothelial cell growth factor (VEGF), platelet derived growth factor (PDGF), insulin-like growth factors (IGF-I and IGF-II), nerve growth factor (NGF), epidermal growth factor (EGF) and heparin-binding EGF-like growth factor (HBEGF). Because of their ability to stimulate cell growth and proliferation, growth factors have been used as wound healing agents. Some growth factors, such as bFGF and VEGF exhibit potent angiogenic effects, i.e. they stimulate the growth of new capillary vessels. These angiogenic growth factors have been used to treat conditions associated with ischemia, such as coronary artery disease and peripheral vascular disease. By treating ischemic tissue with an angiogenic growth factor, new blood vessels are generated which are capable of bypassing occluded segments of arteries, thereby reestablishing blood flow to the affected tissue (a procedure sometimes referred to as a "bio-bypass"). Angiogenic growth factors have also been used to promote wound healing.

A major challenge in the use of growth factors is the development of a delivery vehicle which will provide the appropriate level of bioavailability of the drug to the affected area to achieve a desired clinical result. Hence, U.S. Pat. No. 5,457,093 discloses the use of various agents to produce relatively high viscosity hydrogels containing growth factors. We have found, however, that the use of a hydrogel containing bFGF and hydroxyethyl cellulose failed to produce a desired result in a human clinical trial directed at topical wound healing despite the fact that bFGF is a potent angiogenic agent and possesses other biological activities that are desirable in a wound healing agent. Additionally, we have found that the use of a hydrogel containing bFGF and a polyoxyethylene-polyoxypropylene block copolymer (Pluronic) in an animal model of angiogenesis failed to produce a desired angiogenic response.

Another problem that has been encountered in the preparation of controlled release formulations of polypeptide growth factors is that the excipients employed to impart controlled release characteristics may make it difficult to prepare an homogeneous dispersion of the growth factor by simple mixing techniques. For example, a topical formulation of PDGF has been produced commercially using greater than 1% carboxymethylcellulose. At such concentrations, obtainment of an homogeneous dispersion of the polypeptide is difficult.

It is an object of the invention to provide a formulation for the controlled release delivery of polypeptide growth factors which releases the growth factor at a rate which promotes angiogenesis and/or wound healing.

It is another object of the invention to provide methods for administering growth factors at controlled rates capable of promoting wound healing and/or angiogenesis in a subject in need of such treatment.

It is a further object of the invention to provide controlled release for formulations of polypeptide growth factors that can be prepared as homogeneous compositions by simple mixing techniques.

Other objects of the invention will be apparent from the description which follows.

SUMMARY OF THE INVENTION

In accordance with the present invention, there is provided a hydrogel composition for the controlled release delivery of a polypeptide growth factor comprising:

(a) a therapeutically effective amount of a polypeptide growth factor having at least one region of positive charge;

(b) a physiologically acceptable water-miscible anionic polymer;

(c) a physiologically acceptable water-miscible non-ionic polymeric viscosity controlling agent; and (d) water.

We have discovered that the use of an anionic polymer in combination with a non-ionic polymeric viscosity controlling agent allows one to control independently the drug release characteristics and the physical characteristics, i.e. viscosity, of the formulation. In particular, we have discovered that the water-miscible anionic polymer can be used to impart a therapeutically efficacious release rate when used at low concentrations. Preferably, the water-miscible anionic polymer is selected from sodium carboxymethylcellulose and poly(acrylic acid). Poly(acrylic acid) imparts a therapeutically efficacious release rate when it constitutes as little as 0.001% to 0.01% by weight of the total hydrogel composition. At this low concentration, poly(acrylic acid) does not contribute significantly to an increase in viscosity of the formulation. Thus, one can use the poly(acrylic acid) to optimize the release rate of the growth factor in order to obtain a desired biological effect while employing the physiologically acceptable non-ionic polymer to obtain a desired viscosity for use in a particular application. While one may produce a highly viscous hydrogel in accordance with the invention, we have found that high viscosity is not necessary in order to obtain a desired biological effect in wound healing or angiogenesis.

In one embodiment of the invention, there is provided a method for treating a condition characterized by ischemia wherein the composition of the invention is employed to administer a controlled release dosage of an angiogenic growth factor such as bFGF or VEGF to the ischemic tissue. This method can be used, for example, to treat coronary artery disease or peripheral vascular disease.

In another embodiment of the invention, there is provided a method for promoting wound healing wherein the composition of the invention is employed to administer a controlled release dosage of a growth factor to the wound site.

DETAILED DESCRIPTION OF THE INVENTION

Figure 1:
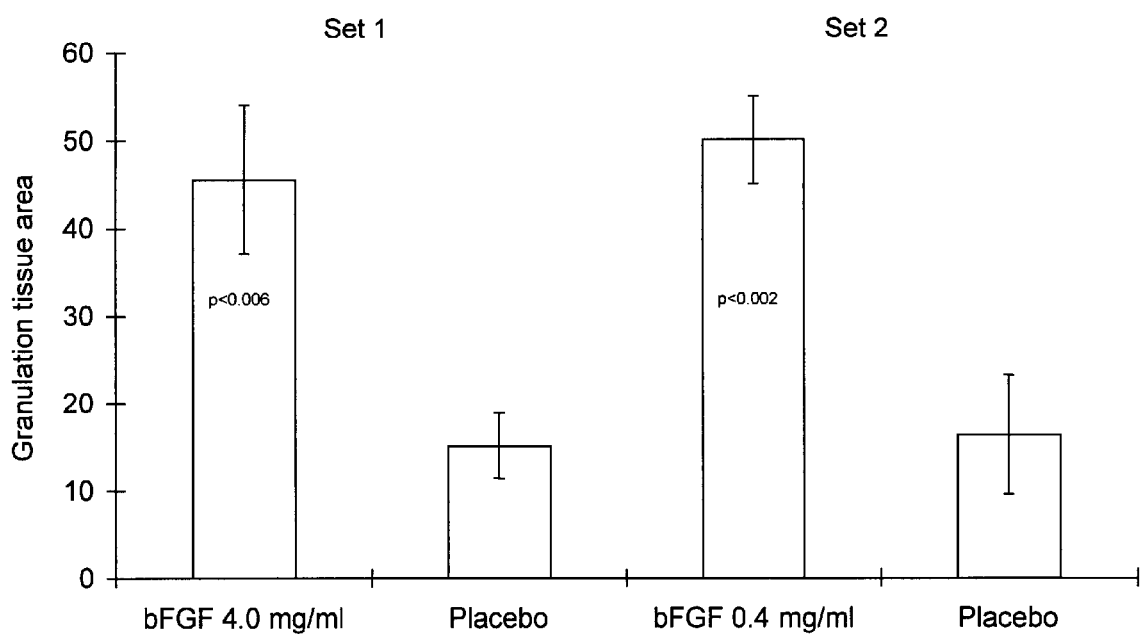
FIG. 1 is a graphic representation of the effect of a bFGF-containing hydrogel formulation of the invention on granulation tissue accumulation in an ischemic rabbit ear wound healing model.

The compositions of the invention can be used for the controlled release delivery of a polypeptide growth factor having at least one region of net positive charge. By "at least one region of net positive charge" is meant that the polypeptide growth factor has a net overall positive charge or has at least one positively charged domain which is capable of interacting with the anionic polymer in such a way as to attenuate the release of the growth factor from the composition. Merely by way of example, one can mention as growth factors suitable for use in the composition of the invention basic fibroblast growth factor (bFGF, including without the limitation the 155-, 154- and 146-amino acid forms), vascular endothelial cell growth factor (VEGF, including without limitation the 189-, 165-, 145-, 121- and 110-amino acid forms), platelet derived growth factor (PDGF), epidermal growth factor (EGF) and heparin binding EGF-like growth factor (HB-EGF). The human amino acid sequences are known for all of these growth factors. VEGF and bFGF belong to a class of growth factors which exhibit angiogenic effects, i.e. they promote the growth of new capillary blood vessels. The process of angiogenesis is an important component of wound healing. Additionally, these polypeptides have been employed to treat conditions characterized by ischemia. Administration of an angiogenic factor to ischemic tissue causes the formation of new capillaries which can bypass an obstructed artery and reestablish blood flow to the affected tissue.

The polypeptide growth factor is employed in a therapeutically effective amount. The specific amount of growth factor employed in the composition will vary with the specific growth factor, the condition being treated and the dosing regimen. Those of ordinary skill in the art will be able to determine an appropriate amount of growth factor to employ in the composition. Generally, the amount may vary from about 0.01% to about 5% by weight of the composition.

The composition of the invention also contains a physiologically acceptable water-miscible anionic polymer. Suitable polymers include, by way of example, poly(acrylic acid), sodium carboxymethylcellulose, alginic acid and hyaluronic acid. Poly(acrylic acid) and sodium carboxymethylcellulose are preferred anionic polymers, with poly (acrylic acid) being most preferred. The anionic polymer employed may have a molecular weight from about 5,000 Da to about 5,000,000 Da.

Generally, the water-miscible anionic polymer can be employed in an amount from about 0.001% to about 1% based on the total weight of the composition. The amount of water-miscible anionic polymer employed in the composition may vary depending, in part, on the specific polymer employed. Since the charge density of the anionic polymer is a determinative factor in the release rate, anionic polymers having a relatively high charge density (and a concomitantly stronger interaction with the polypeptide growth factor) can be employed at lower concentrations in the formulation and still provide effective control over release rate. For example, sodium carboxymethylcellulose has a lower density of negative charge than poly(acrylic acid). Accordingly, poly (acrylic acid) can be effectively employed at considerably lower concentrations than sodium carboxymethylcellulose.

When using poly(acrylic acid) as the water-miscible anionic polymer, it is preferred to employ the poly(acrylic acid) at low concentrations; i.e. from about 0.001% to about 0.1% by weight of the composition. Surprisingly, we have found that the poly(acrylic acid) at these low concentrations is capable of effecting release at a rate which promotes a desirable biological response. Higher poly(acrylic acid) concentrations, i.e. as high as about 1.0%, which also cause a positive biological response, were found to be also associated with an inflammatory response. Furthermore, at higher concentrations, poly(acrylic acid) may contribute to the viscosity of the composition.

Due to its lower charge density, sodium carboxymethylcellulose is preferably employed at a somewhat higher concentration, i.e. from about 0.1% to about 1% based on the total weight of the composition.

The composition of the invention also contains a physiologically acceptable non-ionic polymeric viscosity controlling agent. The non-ionic polymeric viscosity controlling agent can have a molecular weight from about 5,000 Da to about 15,000 Da.

A preferred non-ionic polymeric viscosity controlling agent is a polyoxyethylene-polyoxypropylene block copolymer. Such copolymers consist of segments, or blocks, of polymerized ethylene oxide units, and segments, or blocks, of polymerized propylene oxide units. They are commercially available in a range of molecular weights suitable for use in the compositions of the invention. For example, we have employed a block copolymer of the A-B-A type (polyethylene oxide-polypropylene oxide-polyethylene oxide) having a molecular weight of about 12,600, which is commercially available under the trademark Pluronic® F-127. Such a copolymer provides the advantage that its viscosity increases with temperature. Accordingly, one can prepare a composition of the invention which is relatively free-flowing at room temperature and easily prepared by mixing but increases in viscosity when exposed to body temperature, thereby preventing the composition from flowing away from the desired area of application.

The amount of the polymeric viscosity controlling agent employed may vary considerably depending on the desired viscosity for the particular application. We have found that obtaining satisfactory controlled release of the growth factor does not depend on the viscosity of the composition (although increased viscosity may slow the release rate). The compositions of the invention can range from free-flowing liquids to viscous gels at room temperature. The polymeric viscosity controlling agent may be present from about 0.5% to about 25% by weight of the total composition, preferably 5 to 20%. For some applications, such as topical wound healing, relatively high viscosity may be desired in order to prevent migration of the growth factor from the treatment area. For such applications, one would employ a sufficient amount of the non-ionic polymeric viscosity controlling polymer such that the composition will remain in place at the site of applications.

The compositions of the invention may also contain other conventional pharmaceutical excipients and additives in the usual effective amounts. These may include, for example, preservatives, anti-microbial agents, buffering agents, tonicity agents, surfactants, anti-oxidants, chelating agents and protein stabilizers (e.g., sugars).

The formulations of the invention can be produced by mixing the ingredients. Advantageously, a stock gel may be produced by mixing the non-ionic, polymeric viscosity controlling agent, at the desired concentration, by simple mixing. The anionic polymer is then dissolved in the stock gel solution and an aqueous solution of the growth factor is then dissolved in the gel and/or the gel can be used to reconstitute a freeze dried powder containing growth factor.

The compositions of the invention are useful in promoting wound healing in an individual, e.g. a human or other mammal. The wounds that can be treated with the compositions of the invention include any wounds caused by accidental injury, surgical trauma or disease processes. These include cutaneous wounds such as burn wounds, incisional wounds, donor site wounds from skin transplants, ulcers, including pressure sores, venous stasis ulcers and diabetic ulcers; ophthalmic wounds such as corneal ulcers, radial keratotomy, corneal transplant, epikeratophakia and other surgically induced ophthalmic wounds; and internal wounds such as internal surgical wounds and ulcers.

Application of the composition to the wound site may be performed in a variety of ways, depending on the type of the wound and the consistency of the composition. In the case of a relatively viscous composition, the composition may be applied in the manner of a salve or ointment. In the case of more free-flowing composition, the composition may also be applied by injection or as drops, e.g. eye drops. The composition may also be employed to impregnate a dressing material, in the case of topical application, or an implant material, preferably a biodegradable implant material, in the case of application for internal wound healing. The composition may be delivered in a single application or in multiple applications as needed to deliver a therapeutic dosage, as determined by the wound healing response.

Compositions of the invention containing angiogenic growth factors, e.g. bFGF or VEGF, can be used to treat conditions characterized by ischemia in order to restore blood flow to the affected area. Such conditions include coronary artery disease and peripheral vascular disease. The composition is applied to the affected tissue, for example by injection into the desired area or by use of an implant, in a single or multiple application as needed to achieve a therapeutic dose, as determined by the angiogenic response.

The following examples are provided in order to further illustrate the practice of the invention and are not intended to limit the scope of the invention in any way.

EXAMPLES

In the following examples, the sodium carboxymethylcellulose (CMC) employed had a molecular weight of 70,000 Da. The poly(acrylic acid) had a molecular weight of 3,000,000 Da (sold under the trademark Carbopol®). The polyoxyethylene-polyoxypropylene block copolymer employed as a copolymer of the A-B-A type (polyoxyethylene-polyoxypropylene-polyoxyethylene) having a molecular weight of 12,600 (sold under the trademark Pluronic® 127). The basic fibroblast growth factor (bFGF) employed was recombinantly produced human basic fibroblast growth factor, the expression product of a gene encoding the 155-amino acid form of the protein.

Example 1
Gel Formulation Preparation
1. Preparation of 11.25% Polyoxyethylene-polyoxypropylene Stock Solution In a 250 mL volumetric flask, 28.125 g of polyoxyethylene-polyoxypropylene was dissolved in a 20 mM citrate buffer with 1 mM EDTA (pH 6.0). The solution was mixed by agitation and placed in a 4° C. refrigerator until the polymer was dissolved completely.

2. Preparation of 0.9% CMC and 11.25% Polyoxyethylene-polyoxypropylene Stock Gel Solution In a glass bottle, 0.9 g of sodium carboxymethylcellulose was dissolved in 100 mL of 11.25% polyoxyethylene-polyoxypropylene stock gel solution prepared as described above. The solution was mixed by agitation and placed in a 4° C. refrigerator.

3. Preparation of 0.001% Poly(Acrylic Acid) and 11.25% Polyoxyethylene-polyoxypropylene Stock Gel Solution In a glass bottle, 1 mg of poly(acrylic acid) was dissolved in 100 mL of 11.25% polyoxyethylene-polyoxypropylene stock gel solution prepared as described above. The solution was mixed by agitation and placed in a 4° C. refrigerator.

4. Preparation of a 4.0 mg/mL bFGF Gel Formulation in 10% Polyoxyethylene-polyoxypropylene and 0.8% Sodium Carboxymethylcellulose One vial of lyophilized bFGF (7.2 mg/vial) was reconstituted with 1.6 mL (1.8 mL total volume) of the stock gel solution (0.9% CMC and 11.25% polyoxyethylene-polyoxypropylene) to give a gel formulation with 4.0 mg/mL bFGF, 10% polyoxyethylene-polyoxypropylene and 0.8% CMC. The formulation was mixed by agitation until the powder was completely dissolved.

5. Preparation of 0.4 mg/mL bFGF Gel Formulation in 10% Polyoxyethylene-polyoxypropylene and 0.8% CMC One vial of lyophilized bFGF (7.2 mg/vial) was reconstituted with 1.8 mL (2.0 mL total volume) of water. One mL of the reconstituted of bFGF solution was added to 8.0 mL of the stock gel solution (0.9% CMC and 11.25% polyoxyethylene-polyoxypropylene) to give a gel formulation with 0.4 mg/mL bFGF, 10% polyoxyethylene-polyoxypropylene and 0.8% CMC. The gel formulation was mixed by agitation until the powder was completely dissolved.

6. Preparation of 4.0 mg/mL bFGF Gel in 10% Polyoxyethylene-polyoxypropylene and 0.01% Poly(Acrylic Acid)

The preparation procedure was the same as the preparation of 4.0 mg/mL bFGF gel formulation in 10% polyoxyethylene-polyoxypropylene and 0.8% CMC except the stock gel formulation was 0.01% poly(acrylic acid) and 11.25% polyoxyethylene-polyoxypropylene.

7. Preparation of 0.4 mg/mL bFGF Gel in 10% Polyoxyethylene-polyoxypropylene and 0.01% Poly(Acrylic Acid)

The preparation procedure was the same as the preparation of 0.4 mg/mL bFGF gel formulation in 10% polyoxyethylene-polyoxypropylene and 0.8% CMC except that the stock gel formulation was 0.01% poly(acrylic acid) and 11.25% polyoxyethylene-polyoxypropylene.

Using the procedures described in this Example 1, one can prepare formulations of the invention containing varying amounts of growth factor, water-miscible anionic polymer and water-miscible non-ionic polymer.

Example 2
Promotion of Angiogenesis

Male and female Sprague-Dawley rats (225–425 g body weight) were briefly anesthetized by inhalation of isoflurane. The abdominal area was shaved and cleaned with 70% ethanol. Using an 18- or 25-gauge needle, gel formulations containing varying dosages of bFGF, produced by procedures as described in Example 1, as well as control gel formulations containing no bFGF, were injected subcutaneously along the mid-line of the abdominal area. Animals were alert and mobile almost immediately after inhalation of isoflurane was discontinued.

Five days after injection, animals were euthanized by carbon dioxide inhalation or phenobarbital overdose. Body weight was recorded and the abdominal skin was gently incised and reflected to expose the abdominal muscle. The tissue immediately surrounding the injection site was rated for angiogenesis, as well as for presence or absence of inflammation. The scoring system was as follows:

++++ Substantial angiogenesis
+++ Moderate angiogenesis
+++ Slight angiogenesis
+ Very slight angiogenesis
− No angiogenesis
I Inflammation Results of the 5-day angiogenesis tests are presented in the table below.

Angiogenesis Result of bFGF Gel Formulations (5 days test)

| bFGF (mg/mL) | Polyoxyethylene-Polyoxypropylene (Pluronic 127) | Anionic Polymer | Result |
|---|---|---|---|
| 0.4 | 17% | | − |
| 4.0 | 10% | 0.80% CMC | ++++ |
| 0.4 | 10% | 0.80% CMC | +++ |
| 0.04 | 10% | 0.80% CMC | ++ |
| 0 | 10% | 0.80% CMC | − |
| 0.4 | 15% | 0.50% PAA | ++++,I |
| 0.4 | 10% | 0.78% PAA | ++++,I |
| 4.0 | 10% | 0.80% PAA | +++++,I |
| 0.4 | 10% | 0.80% PAA | ++++,I |
| 0.04 | 10% | 0.80% PAA | ++++,I |
| 0 | 10% | 0.80% PAA | +,I |
| 0.4 | 10% | 0.25% PAA | +++,I |
| 0.4 | 10% | 0.10% PAA | +++,I |
| 0 | 10% | 0.25% PAA | +,I |
| 0 | 10% | 0.10% PAA | +,I |
| 0.4 | 10% | 0.01% PAA | +++ |
| 0.4 | 10% | 0.001% PAA | +++ |
| 0 | 10% | 0.01% PAA | − |
| 0 | 10% | 0.001% PAA | − |

PAA = poly(acrylic acid)
CMC = sodium carboxymethylcellulose

Example 3
Promotion of Wound Healing

Dr. Thomas Mustoe (Division of Plastic Surgery and Departments of Surgery and Pathology, Northwestern University Medical School, Chicago) has demonstrated that ischemia in the rabbit ear, induced by surgical transection of two of the three major ear arteries, results in impaired healing of full thickness skin wounds (Ahn and Mustoe, *Ann Plast Surg* 24:17–23 (1990)). As the wound is splinted by the underlying intact cartilage of the ear, wound closure occurs by cellular infiltration and not by physical contraction. Published studies have shown that bFGF administered in saline at doses up to 30 µg/wound is ineffective in stimulating the accumulation of granulation tissue or epithelial tissue in these wounds (Wu et al., *Growth Factors* 12:29–35 (1995)). The effects of bFGF delivered in a sustained release gel formulation was tested in this model.

Figure 2:
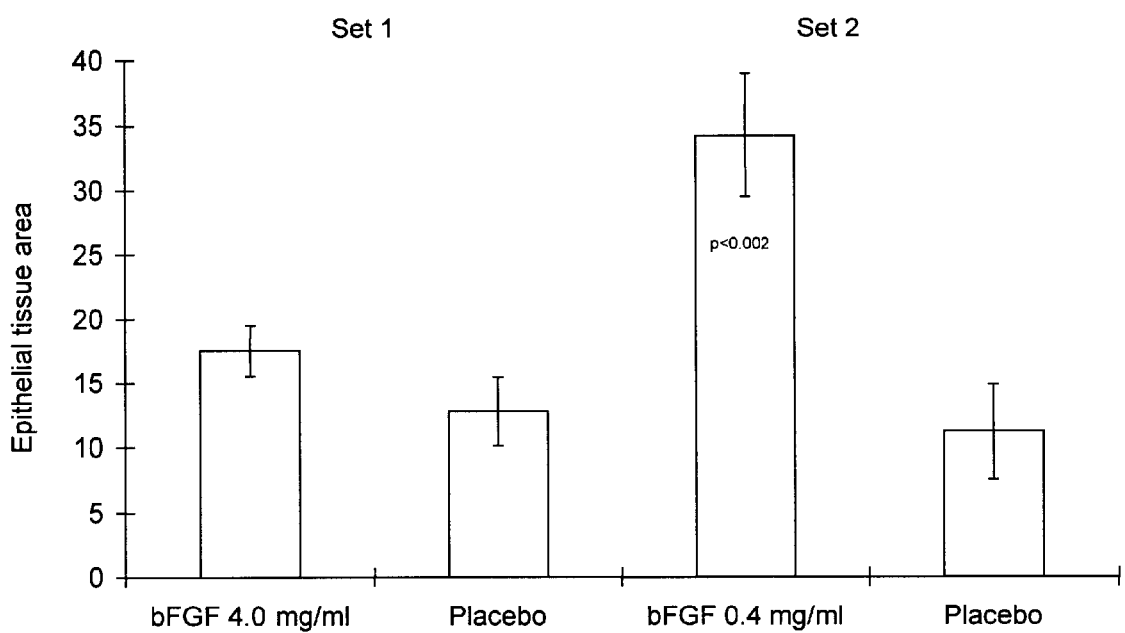
FIG. 2 is a graphic representation of the effect of a bFGF-containing hydrogel formulation of the invention on epitheleal tissue accumulation in an ischemic rabbit ear wound healing model.
Figure 3:
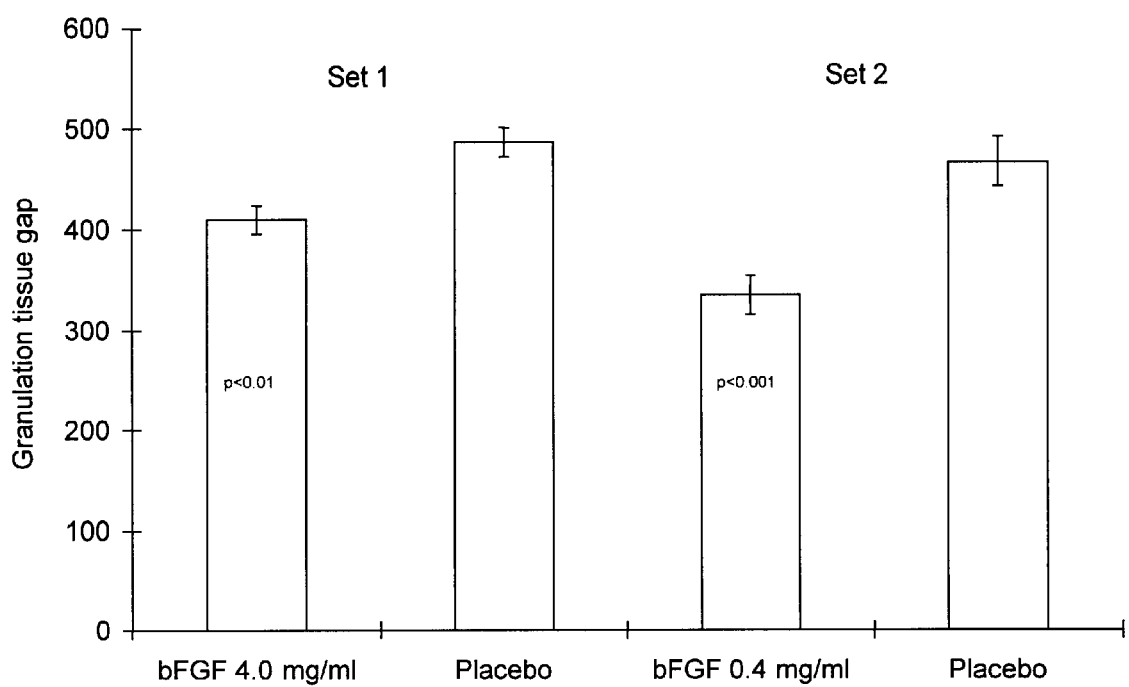
FIG. 3 is a graphic representation of the effect of a bFGF-containing hydrogel formulation of the invention on granulation tissue gap in ischemic rabbit ear wounds.
Figure 4:
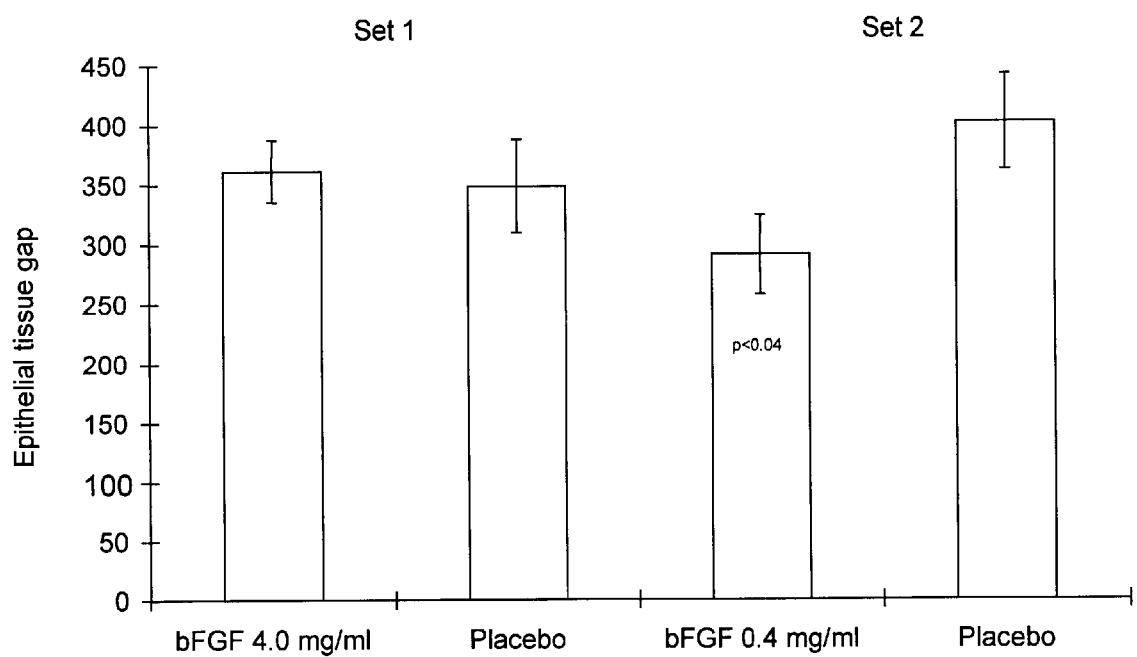
FIG. 4 is a graphic representation of the effect of a bFGF-containing hydrogel formulation of the invention on epithelial tissue gap in ischemic rabbit ear wounds.

Two dosage forms of bFGF (0.4 mg/mL and 4.0 mg/mL) formulated with 10% polyoxyethylene-polyoxypropylene (Pluronic® 127) plus 0.001% polyacrylic acid were tested with placebo controls (formulation without bFGF) in a blinded manner. Each dosage form was applied at 10 µL per wound (4 and 40 µg/wound bFGF). Test samples were applied once on the day the wound was made. Histological assessment, made after 7 days of recovery, included quantitation of granulation tissue and epithelial tissue accumulation (Wu et al., 1995). There was a significant accumulation of granulation tissue (represented in FIG. 1) and epithelial tissue (represented in FIG. 2) in the wound area in response to bFGF. In addition, the wound size, measured in terms of the granulation tissue gap (represented in FIG. 3) and the epithelial tissue gap (represented in FIG. 4) was reduced in a statistically significant manner by bFGF treatment using the formulation of the invention. The P values indicated in FIGS. 1–4 were derived by a two-tailed unpaired t-test. Previous work has shown that doses of bFGF up to 30 µg/wound formulated in saline were ineffective in this model.

Example 4
In vitro Release of bFGF

Figure 5:
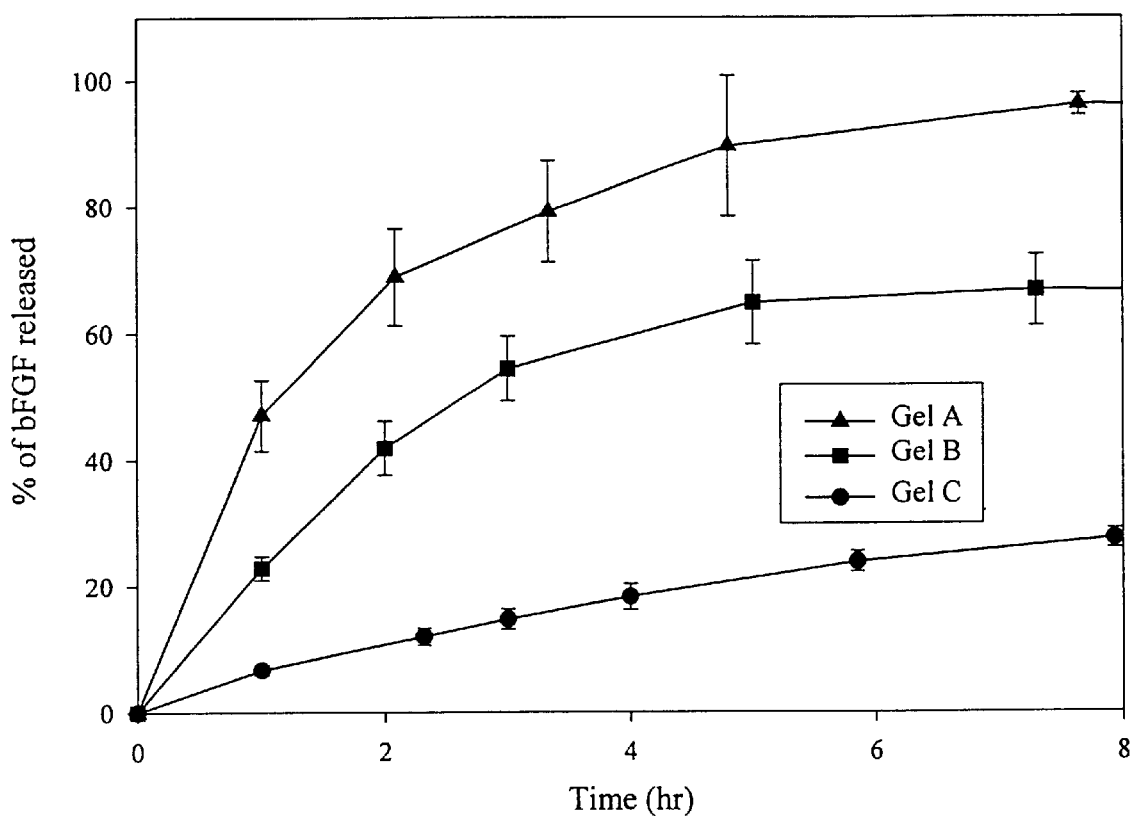
FIG. 5 illustrates the release of bFGF from gel formulations containing 0.4 mg/mL bFGF. A: 10% Pluronic® and 0.8% CMC; B: 10% Pluronic® and 0.001% Carbopol®; C: 10% Pluronic®.
Figure 6:
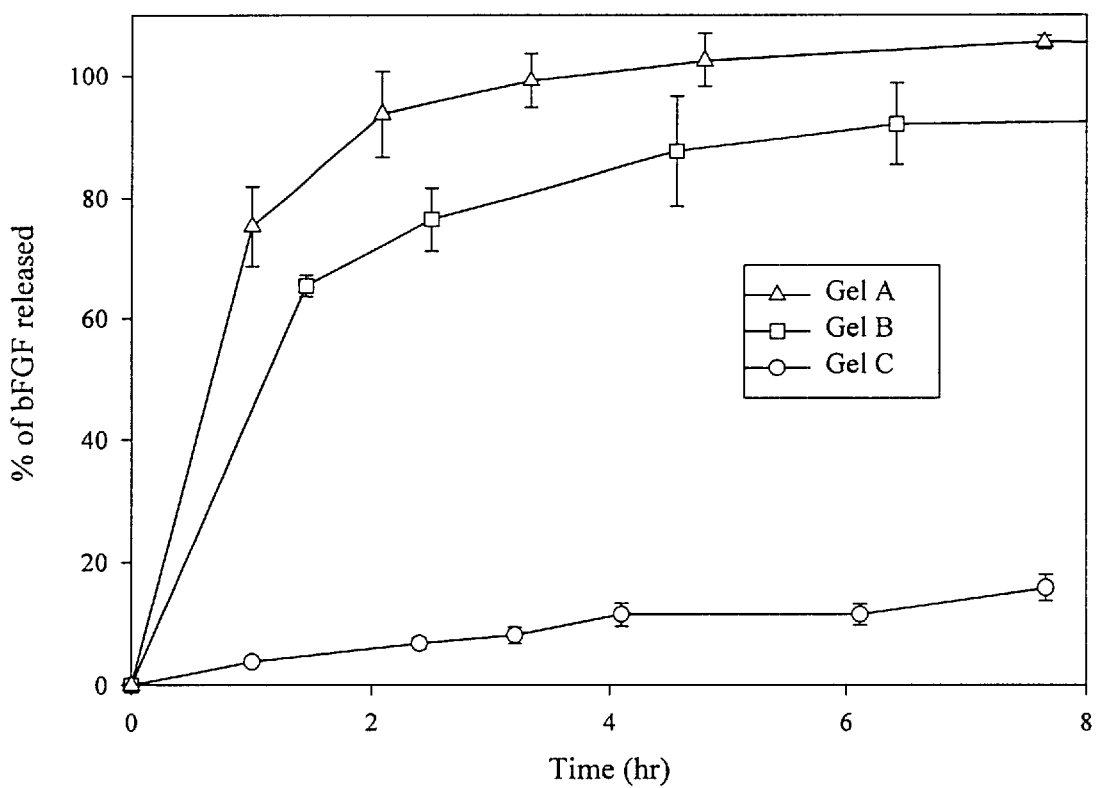
FIG. 6 illustrates the release of bFGF from gel formulations containing 4.0 mg/mL bFGF. A: 10% Pluronic® and 0.8% CMC; B: 10% Pluronic® and 0.001% Carbopol®; C: 10% Pluronic®.

The in vitro release of bFGF from various gel formulations was evaluated using Franz diffusion cells (Model FDC40015FG, Crown Bioscientific, Inc., N.J.) at 32° C. Each cell consists of a donor and receiving chamber. A hydrophilic membrane (Nucleopore Track-Etch Membrane, Corning Separation Division, No. 110609) was mounted between the donor and receiving chambers. The membrane was chosen to allow bFGF, but no significant amounts of Pluronic®, Carbopol®, or sodium CMC to cross into the receiving chamber. Gel formulations were placed in the donor chamber and a buffer solution (100 g/ml heparin in HBS-EP buffer [BIA certified, Biacore AB, Uppsala, Sweden, containing 0.01M HEPES at pH 7.4, 0.15 M NaCl, 3 mM EDTA and 0.05% Polysorbate 20]) was placed in the receiving chamber. Samples were withdrawn from the receiving chamber at various times and the bFGF concentrations were determined using a BiaCore 2000 instrument (Biacore AB, Uppsala, Sweden). The cumulative amount and cumulative percent released were then calculated, and the results are shown in FIGS. 5 and 6, respectively.

What is claimed is:

1. A hydrogel composition for the controlled release delivery of a polypeptide growth factor comprising:

(a) a therapeutically effective amount of a polypeptide growth factor containing at least one region of positive charge;

(b) a physiologically acceptable water-miscible anionic polymer;

(c) a physiologically acceptable water-miscible non-ionic polymeric viscosity controlling agent; and (d) water.

2. A composition as claimed in claim 1, wherein said growth factor is selected from basic fibroblast growth factor, platelet derived growth factor, epidermal growth factor, vascular endothelial cell growth factor and heparin binding EGF (HBEGF) growth factor.

3. A composition as claimed in claim 1, wherein said growth factor is basic fibroblast growth factor.

4. A composition as claimed in claim 1, wherein said water-miscible anionic polymer is selected from sodium carboxymethylcellulose and poly(acrylic acid).

5. A composition as claimed in claim 1, wherein said water-miscible anionic polymer is poly(acrylic acid).

6. A composition as claimed in claim 1, wherein said water-miscible non-ionic polymeric viscosity controlling agent is a polyoxyethylene-polyoxypropylene block copolymer having a molecular weight from 5,000 Da to about 15,000 Da.

7. A composition as claimed in claim 1, wherein said anionic polymer is present in an amount from about 0.001% to about 1.0% by weight of said composition.

8. A composition as claimed in claim 5, wherein said poly(acrylic acid) is present in an amount from about 0.001% to about 0.1% by weight of said composition.

9. A composition as claimed in claim 5, wherein said poly(acrylic acid) is present in an amount from about 0.001% to about 0.01% by weight of said composition.

10. A composition as claimed in claim 6, wherein said non-ionic polymeric viscosity controlling agent is present in an amount from about 0.5% to about 25% by weight of said composition.

11. A hydrogel composition for the controlled release administration of basic fibroblast growth factor, which comprises:
   (a) a therapeutically effective amount of basic fibroblast growth factor;
   (b) from about 0.001% to about 0.1% by weight physiologically acceptable, water-miscible anionic polymer;
   (c) from about 0.5% to about 25% by weight non-ionic, water-miscible polymeric viscosity controlling agent; and
   (d) water.

12. A method for the controlled release delivery of a growth factor comprising administering to an individual in need of treatment with such growth factor a hydrogel composition comprising:
   (a) a therapeutically effective amount of a polypeptide growth factor having at least one region of positive charge;
   (b) a physiologically acceptable water-miscible anionic polymer;
   (c) a physiologically acceptable water-miscible non-ionic polymeric viscosity controlling agent; and
   (d) water.

13. A method as claimed in claim 12, wherein said growth factor is selected from basic fibroblast growth factor, platelet derived growth factor, epidermal growth factor, vascular endothelial cell growth factor and heparin binding EGF (HBEGF) growth factor.

14. A method as claimed in claim 12, wherein said growth factor is basic fibroblast growth factor.

15. A method as claimed in claim 12, wherein said anionic polymer is selected from sodium carboxymethylcellulose and poly(acrylic acid).

16. A method as claimed in claim 12, wherein said non-ionic polymeric viscosity controlling agent is a polyoxyethylene-polyoxypropylene block copolymer.

17. A method as claimed in claim 12, wherein the anionic polymer is present in an amount from about 0.001% to about 0.1% by weight of the composition.

18. A method as claimed in claim 12, wherein the non-ionic polymeric viscosity controlling agent is present in an amount from about 0.5% to about 25% by weight of the composition.

19. A method for promoting wound healing which comprises administering to an individual in need of such treatment of a controlled release hydrogel composition comprising:
   (a) a therapeutically effective amount of basic fibroblast growth factor;
   (b) from about 0.001% to about 0.1% by weight physiologically acceptable, water-miscible anionic polymer;
   (c) from about 0.5% to about 25% by weight non-ionic, water-miscible polymeric viscosity controlling agent; and
   (d) water.

20. A method as claimed in claim 12, wherein the hydrogel composition is administered by depot injection.

21. A method as claimed in claim 12, wherein the hydrogel composition is administered topically.

22. A method for producing a controlled release growth factor composition which comprises dispersing in water:
   (a) a physiologically acceptable, water miscible, non-ionic polymeric viscosity controlling agent;
   (b) a sufficient amount of a physiologically acceptable, water miscible, anionic polymer to impart controlled release of the growth factor from the composition; and
   (c) a therapeutically effective amount of polypeptide growth factor having at least one region of positive charge.

23. A method of treating ischemia which comprises administering to a region of ischemic tissue in a subject suffering from a condition characterized by ischemia a controlled release hydrogel composition comprising:
   (a) a therapeutically effective amount of an angiogenic polypeptide growth factor having at least one region of positive charge;
   (b) a physiologically acceptable water-miscible anionic polymer;
   (c) a physiologically acceptable water-miscible non-ionic polymeric viscosity controlling agent; and
   (d) water.

24. A method as claimed in claim 23, wherein said angiogenic polypeptide growth factor is selected from basic fibroblast growth factor and vascular endothelial cell growth factor.

25. A method as claimed in claim 23, wherein said angiogenic polypeptide growth factor is basic fibroblast growth factor.

26. A method as claimed in claim 23, wherein said growth factor is basic fibroblast growth factor.

27. A method as claimed in claim 23, wherein said water-miscible anionic polymer is selected from sodium carboxymethylcellulose and poly(acrylic acid).

28. A method as claimed in claim 23, wherein said water-miscible anionic polymer is poly(acrylic acid).

29. A method as claimed in claim 23, wherein said water-miscible non-ionic polymeric viscosity controlling agent is a polyoxyethylene-polyoxypropylene block copolymer having a molecular weight from about 5,000 Da to about 15,000 Da.

30. A method as claimed in claim 23, wherein said anionic polymer is present in an amount from about 0.001% to about 0.1% by weight of said composition.

31. A method as claimed in claim 23, wherein said non-ionic polymeric viscosity controlling agent is present in an amount from about 0.5% to about 25% by weight of said composition.

32. A method as claimed in claim 23, wherein the ischemic condition being treated is peripheral vascular disease.

33. A method as claimed in claim 23, wherein the ischemic condition being treated is coronary artery disease.

34. A method as claimed in claim 32, wherein the angiogenic growth factor is selected from basic fibroblast growth factor and vascular endothelial cell growth factor.

35. A method as claimed in claim 33, wherein the angiogenic growth factor is selected from basic fibroblast growth factor and vascular endothelial cell growth factor.

36. A method as claimed in claim 33, wherein the angiogenic growth factor is basic fibroblast growth factor.

37. A method as claimed in claim 33, wherein the angiogenic growth factor is basic fibroblast growth factor.

* * * * *